United States Patent [19]
Balducci et al.

[11] Patent Number: 5,965,476
[45] Date of Patent: *Oct. 12, 1999

[54] SILICA/ZEOLITE COMPOSITE MATERIALS IN SPHERICAL FORM AND PROCESS FOR THEIR PREPARATION

[75] Inventors: Luigi Balducci, Mortara; Raffaele Ungarelli, Trecate; Cristina Tonini, Pernate, all of Italy

[73] Assignee: Enichem S.p.A., Milan, Italy

[*] Notice: This patent issued on a continued prosecution application filed under 37 CFR 1.53(d), and is subject to the twenty year patent term provisions of 35 U.S.C. 154(a)(2).

[21] Appl. No.: 08/801,593

[22] Filed: Feb. 14, 1997

[30] Foreign Application Priority Data

Feb. 22, 1996 [IT] Italy ............... MI 96 A 0330
Jun. 9, 1996 [IT] Italy ............... MI 96 A 1836

[51] Int. Cl.$^6$ ..................................... B01J 32/00
[52] U.S. Cl. ................ 502/67; 502/8; 549/531; 568/803
[58] Field of Search ............... 502/60, 63, 64, 502/67, 68, 8

[56] References Cited

U.S. PATENT DOCUMENTS 5,270,027  12/1993  Balducci et al. .

FOREIGN PATENT DOCUMENTS 0 243 629   11/1987  European Pat. Off. .
0 350 549    1/1990  European Pat. Off. .
2 471 950    6/1981  France .
42 40 693    6/1994  Germany .
WO 89/04860  6/1989  WIPO .

OTHER PUBLICATIONS

Database WPI, Derwent Publications, AN 83–841228, JP–58–189039, Nov. 4, 1983.

*Primary Examiner*—Michael L. Shippen
*Attorney, Agent, or Firm*—Oblon, Spivak, McClelland, Maier & Neustadt, P.C.

[57] ABSTRACT

The present invention relates to silica/zeolite composite materials in spherical form and the process for their preparation which occurs by the dispersion of submicronic particles of titanium silicalite, beta zeolite, or mixtures of beta zeolite with titanium silicalite, in a silica sol synthesized by acid hydrolysis of silicon alkoxides; the hybrid sol thus obtained, subjected to emulsification and gelation techniques in organic mediums, produces these materials in a spherical form with an average diameter of between 20 and 150 μm and containing up to 70% by weight of titanium silicalite, beta zeolite or mixtures of titanium silicalite/beta zeolite.

The materials of the invention, having a high mechanical resistance and characterized by a surface area of between 300 and 800 m$^2$/g, are applied as catalysts; in particular, those consisting of titanium silicalite or mixtures of titanium silicalite/beta zeolite are advantageously used in oxidation reactions of organic compounds with hydrogen peroxide.

2 Claims, No Drawings

SILICA/ZEOLITE COMPOSITE MATERIALS IN SPHERICAL FORM AND PROCESS FOR THEIR PREPARATION

The present invention relates to silica/zeolite composite materials in spherical form and the process for their preparation.

In particular these materials consist of microspheres of silica/titanium silicalite, silica/beta zeolite or silica/titanium-silicalite/beta zeolite, with a content of zeolitic compounds of less than or equal to 70% by weight and characterized by specific surface values of between 300 and 800 $m^2/g$.

Titanium-silicalites (or TS-1 and homologous products) and beta zeolites form two important groups of catalysts.

In particular, titanium silicalites are crystalline compounds having general formula $xTiO_2(1-x)SiO_2$ with x varying from 0.0005 and 0.04 (U.S. Pat. No. 4,010,501); using hydrogen peroxide as oxidating agent, they have a particular selectivity in epoxidation reactions of olefins, hydroxylation reactions of aromatic compounds, oxidation reactions of alcohols and amines and amoxymation reactions of ketones [Chim. & Ind., 72(1990), 610–616].

Beta zeolites, on the other hand, synthesized for the first time by Wadlinger et al. (U.S. Pat. No. 3,308,069) using tetraethyl ammonium hydroxide as templating agent, are crystalline aluminosilicates with a molar ratio $SiO_2/Al_2O_3$ varying from 10 to 200; these compounds are applied as catalysts in petrolchemical processes and in organic syntheses such as the alkylation of benzene with light olefins (U.S. Pat. No. 4,891,458; EP 432.814) or of isobutane with n-butene (FR 2,631,936).

Both titanium-silicalites and beta zeolites, in powder form, consist of individual particles with submicronic dimensions (<1 $\mu$m).

These materials are normally subjected to granulation processes to make them suitable for use in industrial processes; the form and dimensions of the granules are defined each time on the basis of various factors such as, for example, the type of reactor, the need to intervene on mass transport or heat phenomena or to control load losses of the catalytic bed.

If sphericial particles with dimensions which are less than or equal to 100 $\mu$m are requested, the spray drying technique is normally used.

This process however has problems of controlling the physical and mechanical properties of the granules; in fact, hollow microspheres are often obtained with a low apparent density and with a reduced mechanical resistance to external stress such as that deriving from interparticle collision or impact against the stirrer blades or against the walls of the reactor.

This causes difficulty in the separation and recovery of the catalyst (for example poor filtrability) or loss of material (for example fraction of fine non-recyclable particles) depending on the technology used in the catalytic process.

To overcome or minimize these drawbacks, various technological solutions have been proposed, such as spray drying processes in which inert materials are used, combined with titanium silicalite, which act as ligand between the individual particles of the active component.

Silica has proved suitable for the purpose, prepared by the hydrolysis of $Si(OR)_4$ in the presence of tetrapropyl-ammonium hydroxide as described in U.S. Pat. No. 4,859,785 and in U.S. Pat. No. 4,954,653; with these processes catalysts have been prepared in which the content of inert material is maintained at less than or equal to 10% by weight in order not to prejudice the catalytic activity of the titanium silicalite.

Also in these cases, however, the morphological-structural defects of the microspheres, such as cavities, which are known to occur even more frequently with an increase in the particle dimensions, are not completely eliminated.

It has now been found that these drawbacks can be overcome by dispersing submicronic and crystalline particles of titanium silicalite or mixtures of titanium silicalite/beta zeolite in a silica sol thus obtaining a hybrid sol which, when subjected to emulsification and gelation techniques in organic mediums, produce materials with controlled characteristics.

A first object of the present invention therefore relates to silica/titanium silicalite, silica/beta zeolite and silica/titanium silicalite/beta zeolite composite materials, consisting of microspheres with an average diameter of between 20 and 150 $\mu$m, containing up to 70% by weight of the above zeolitic compounds and characterized by specific surface values of between 300 and 800 $m^2/g$.

With respect to the traditional processes for obtaining materials in spherical form (spray drying), the process based on the emulsification and gelation of hybrid silica/zeolite sols, although operating with high contents of silica (higher than or equal to 30% by weight), does not cause structural modifications which can prejudice the catalytic activity of the active components.

It has in fact been found that silica/titanium silicalite composite materials can be advantageously used as catalysts in oxidation reactions with $H_2O_2$, such as for example, epoxidation reactions of olefins, hydroxylation reactions of aromatic compounds, oxidation reactions of alcohols and amines and amoxymation reactions of ketones in the presence of ammonia.

In particular, ternary silica/titanium silicalite/beta zeolite compositions have shown a significant increase in catalytic activity in the hydroxylation reaction of benzene to phenol with respect to titanium silicalite or $SiO_2$/TS-1 composite.

A further object of the present invention therefore relates to a process for the preparation of the above materials, comprising the following steps:

preparation of a silica sol by the acid hydrolysis of silicon alkoxides;

mixing of said sol with an aqueous or hydroalcoholic suspension of particles of titanium silicalite or beta zeolite or mixtures of titanium silicalite/beta zeolite, having dimensions of less than 1 $\mu$m, thus obtaining a hybrid sol;

emulsification and gelation in organic mediums of said hybrid sol.

In the preparation process of the invention it is preferable to use titanium-silicalites of the type $xTiO_2(1-x)SiO_2$ with x varying from 0.01 to 0.035 and beta zeolites characterized by molar ratios $SiO_2/Al_2O_3$ varying from 20 to 30 (alkaline oxides less than 500 ppm); crystalline precursors of these compounds containing the organic base (templating agent), can be advantageously used, thus simplifying the processing cycle of the composite materials.

In addition, crystalline precursors consisting of individual particles with a diameter of less than 1 $\mu$m, are preferably used.

The powders of these precursors are initially disaggregated in water or hydroalcoholic solution in a finely subdivided form by means of, for example, rapid dispersers; rotor-stator types such as Ultraturrax (Ika-Werk) have proved to be particularly efficient for the purpose.

As an alternative to the mechanical disaggregation systems, also ultrasonic systems can also be suitably used.

The disaggregation of the precursors is carried out under such operating conditions as to reduce the average dimensions of the aggregates to values close to those of the individual particles of the material (<1 μm); for this reason, in the case of the preparation of ternary composite materials, it is preferable to carry out the disaggregation of the single components independently and the aqueous or hydroalcoholic suspensions thus obtained are then joined and homogenized.

The concentration of the solids in the aqueous or hydroalcoholic suspension is preferably higher than 10% by weight to avoid excessive dilution of the hybrid sol.

The presence of the templating agent in the precursors gives the aqueous or hydroalcoholic suspension a decisively alkaline pH; to avoid the appearance of undesirable gelation phenomena in the subsequent mixing with the acid silica sol, this suspension is acidified to pH values of less than or equal to 7 and, preferably, under such conditions that the resulting hybrid sol has a pH of between 3.5 and 4.5 extremes included.

The acidification can be carried out with solutions of mineral or organic acids and, under the preferred conditions, with the type of acid used in the preparation of the silica sol.

This operation can be avoided when powders previously subjected to thermal treatment to remove the templating agent, are used in the process.

The aqueous or hydroalcoholic suspension of titanium silicalite or mixtures of titanium-silicalite/beta zeolite, in the subsequent phase of the process, is mixed with a silica sol prepared by the acid hydrolysis of silicon alkoxides, such as for example, tetramethoxy or tetraethoxyorthosilicate, following the known method as described in U.S. Pat. No. 5,270,027.

It is preferable to use silica sols obtained by the hydrolysis of tetraethoxyorthosilicate (TEOS) in a aqueous medium and in the presence of mineral acids, such as for example, HCl, regulating the molar ratio $H_2O$/TEOS to between 16 and 24 and the pH to between 1.5 and 3.0; if the conditions are such that the concentration of $SiO_2$ in the sol is higher than 100 g/l, corresponding to molar ratio values $H_2O$/TEOS<21, the quantity of HCl is regulated so that the molar ratio TEOS/HCl is between 300 and 400.

The hydrolysis reaction is carried out maintaining the reagents under mechanical stirring for times varying from 1 to 3 hours at a maximum temperature of 35° C.

With respect to the preparation of the hybrid sol, the mixing of the silica sol with the aqueous or hydroalcoholic suspension of titanium silicalite or mixtures of titanium silicalite/beta zeolite is carried out with the traditional systems of mechanical stirring or with rapid dispersers, operating at a maximum temperature of 35° C. with times generally less than 15 minutes.

The weight ratio zeolitic compounds/$SiO_2$, compatibly with the morphological-structural characteristics of the microspheres, can be extended up to a value of 2.5 inclusive, thus obtaining composite materials containing up to about 70% by weight of titanium silicalite or beta zeolite or mixtures of titanium-silicalite/beta zeolite.

If the materials are used as catalysts, it is convenient for these to have a content of zeolitic compounds of between 50 and 70% by weight.

With respect to the ternary compositions $SiO_2$/TS-1/zeolite, the weight ratio beta zeolite/titanium-silicalite can vary within a wide range of values depending on the application of the catalyst; in this way, for example, in hydroxylation reactions of benzene to phenol with $H_2O_2$, it has proved advantageous to operate with a weight ratio zeolite/TS-1 varying from 0.3 to 1.6.

The concentration of alcohol in the hybrid sol, and in particular of ethanol deriving from the hydrolysis of TEOS, can be appropriately corrected, for example by distillation, at reduced pressure and a temperatures of less than 30° C. or by the further addition of EtOH, depending on the emulsification conditions adopted in the subsequent process operation; this is to control the interactions between the dispersed phase (hybrid sol) and the continuous phase (organic medium) of the emulsified system.

The hybrid sols thus prepared can be further used in processes for the preparation of composite materials with a spherical morphology using the known emulsification and gelation techniques.

In particular, the procedure followed to illustrate the following invention is described in the patent EP 653.378 and consists in initially emulsifying the sol in an organic medium (decanol) and consolidating the microdrops formed by bringing the emulsion rapidly in contact with a basic solution (cyclohexylamine in decanol).

The microspheres of gel thus obtained are subsequently separated from the emulsifying medium, washed repeatedly with ethanol, dried and finally calcined in an oxidating atmosphere at a temperature of more than 450° C., preferably between 500 and 550° C.

The composite materials prepared from hybrid sols and object of the present invention consist of microspheres with an average diameter of between 20 and 150 μm and with a compact internal structure without cavities; this gives the microspheres a high mechanical resistance, thus minimizing problems relating to the fragility of the particles.

NMR analyses of aluminium-27 ($^{27}Al$) in its solid state have shown that the structural conformation of this element (tetrahedric species) remains basically unaltered also in binary and ternary composite materials, thus confirming the limited influence of the process conditions on the structure of the beta zeolite.

The combination of this compound with titanium silicalite leads to the formation of ternary composite materials which, with respect to the material based on TS-1 alone, have a higher catalytic activity in the hydroxylation reaction of aromatic hydrocarbons with $H_2O_2$; in particular, composite materials characterized by weight ratios beta zeolite/titanium silicalite varying from 0.3 to 1.6, molar ratios Ti/Al varying from 0.3 to 1 and contents of $SiO_2$ varying from 40 to 50% by weight, have proved to be particularly active, in yield and selectivity in the hydroxylation reaction of benzene to phenol.

The composite materials are characterized hereafter in terms of median diameter of the microspheres ($D_{50}$) and surface area (S.S.).

The average dimension of the microspheres was measured by means of a Malvern analyzer Series 2600C (Malvern Instruments, England) and expressed in terms of median diameter ($D_{50}$), corresponding to the diameter of the particles with the ordinate at 50% in the granulometric distribution curve of the microspheres in cumulative form.

The mechanical resistance of the microspheres was evaluated by granulometric measurements carried out before and after the treatment of the powders with ultrasounds; in addition to the value of the median diameter, also the values of the adimensional ratios $(D_{90}-D_{10})/D_{50}$ and $D_{90}/D_{10}$, wherein $D_{90}$ and $D_{10}$ represent the diameters of the microspheres with the ordinate at 90% and 10% respectively in the granulometric distribution curve in cumulative form, were used as evaluation indexes of these properties.

The surface area was determined with the BET method (Brunauer, Emmet and Teller) which is widely known and applied.

The following experimental examples are illustrative and do not limit the scope of the present invention.

EXAMPLE 1

A description follows of the preparation of a silica/titanium silicalite composite material.

A) Preparation of the Hybrid Sol 320 g of TEOS (Aldrich; titer 98%) and 430 ml of demineralized $H_2O$ acidified with 4.5 ml of HCl 1N (molar ratio $H_2O$/TEOS=16) are charged into a 2 liter flask equipped with a mechanical stirrer, thermometer and external cooling bath.

The reagents are maintained under stirring at a temperature of 25–30° C. and for the time necessary for obtaining a limpid solution (about 35 minutes); the stirring is then continued for a further 60 minutes.

The acid silica sol thus obtained (pH 2.6 approximately) is stored in a refrigerator at 5° C. until use.

An intermediate containing the templating agent (tetrapropylammonium hydroxide) prepared according to the process described in U.S. Pat. No. 4,410,501, is used as precursor of the titanium silicalite (TS-1); upon analysis the precursor gave the following results:

titer in TS-1=68%; molar ratio $TiO_2/SiO_2$=0.03.

10.3 g of the above precursor are dispersed in 60 ml of $H_2O$ under magnetic stirring with a teflon-coated rod for 5 minutes and subsequently for a further 10 minutes with an ultrasonic probe (Sonifier, Cell Disruptor B15; Branson); the aqueous suspension of TS-1, consisting of submicronic particles with a median diameter ($D_{50}$) of 0.36 μm, is then acidified with HCl 1N to pH 3.

50 ml of acid silica sol, maintained under magnetic stirring, are diluted with 60 ml of ethanol (99%) and then mixed with 70 g of the aqueous suspension of TS-1 previously prepared; a further dispersion is carried out with an ultrasonic probe for 3 minutes.

B) Preparation of the Composite Material

The preparation of the composite material was carried out according to the process described in the patent EP 653.378 using however a different emulsification technology.

The hybrid sol (about 170 ml) is transferred to a cylindrical reactor (internal diameter 100 mm; volume 1000 ml), previously charged with 500 ml of 1-decanol (Fluka; titer 98%); the stirrer with 6 radial blades is then activated and the rate regulated to 500 revs per minute (r.p.m.).

After 10 minutes, the emulsion is rapidly discharged from the bottom of the reactor into an underlying container containing 300 ml of a solution at 10% (v/v) of cyclohexylamine (Aldrich; titer 99%) in decanol, maintained under mechanical stirring at room temperature.

The stirring is continued for a further 10 minutes, the solid is then left to settle and, in a subsequent phase, is filtered and washed repeatedly with ethanol.

After drying at reduced pressure and at a temperature of less than 30° C., the product is calcined in an oxidating atmosphere (air) at 550° C. for 4 hours, with a heating rate of 50° C./h.

The composite material thus obtained proves to consist of microspheres with the following characteristics:

composition (weight %): TS-1=55; $TiO_2$=2.1;
median diameter ($D_{50}$ in μm): 74;
specific surface (in $m^2$/g): 584.

Scan electronic microscopy (SEM) examinations, carried out on the fracture surface of the microspheres, showed structural uniformity; X-ray diffraction analyses did not show any variation in the crystalline structure of the titanium silicalite.

EXAMPLES 2–4

With respect to example 1, the composition of the hybrid sol is varied, in whose preparation the ratio between the volume of ethanol (added to the silica sol) and that of the aqueous suspension of titanium silicalite has been maintained constant; in all the examples the volume of hybrid sol (170 ml) has been maintained constant.

The composition and characteristics of the products obtained are shown in table 1.

TABLE 1

| EXAMPLE | TS-1(%) | $TiO_2$ (%) | $D_{50}$ (μm) | S.S. ($m^2$/g) |
|---|---|---|---|---|
| 2 | 23.6 | 0.9 | 52 | 483 |
| 3 | 39.3 | 1.5 | 54 | 559 |
| 4 | 48.9 | 1.87 | 57 | 485 |

The composite materials synthesized according to the examples, proved to consist of microspheres whose fracture section, examined with SEM, does not have any structural defects (cavities).

EXAMPLE 5

A description follows of the preparation of a silica/beta zeolite composite material.

An intermediate containing the templating agent (tetraethylammonium hydroxide) is used as precursor of the beta zeolite; upon analysis the precursor gave the following results:

titer in beta zeolite=82.5 weight %;
molar ratio Si/Al=11.55.

8.2 g of the above precursor are dispersed in 60 ml of demineralized $H_2O$ under magnetic stirring for 30 minutes and subsequently for a further 15 minutes with an ultrasonic probe (Sonifier, Cell Disruptor B15; Branson); after dilution with 60 ml of EtOH, the treatment is continued in ultrasounds for a further 10 minutes.

The hydroalcoholic suspension of beta zeolite proves to consist of particles with a median diameter ($D_{50}$) of 0.23 μm.

50 ml of acid silica sol of example 1 are mixed, by magnetic stirring, with the hydroalcoholic suspension of beta zeolite previously prepared.

The hybrid sol thus obtained is maintained under stirring for 3 minutes and then emulsified in the apparatus of example 1, regulating the stirring rate to 800 r.p.m.

The composite material thus obtained proves to consist of microspheres with the following characteristics:

median diameter ($D_{50}$ in μm)=58;
composition (weight % of beta zeolite)=55;
specific surface (S.S. in $m^2$/g):716.

The fracture surface of the particles, examined with a scan electronic microscope (SEM), proved to be compact and without macroscopic structural defects; by means of NMR analysis of aluminium 27 ($^{27}$Al) it was also verified that the spherulization process of the composite material does not alter the structural configuration of the aluminium.

EXAMPLE 6

A description follows of the preparation of a composite material consisting of silica/titanium silicalite/beta zeolite.

5.65 g of the titanium silicalite precursor of example 1 are dispersed in 30 ml of demineralized $H_2O$ under magnetic stirring for 3 minutes and subsequently, for a further 10 minutes, with an ultrasonic probe; the aqueous suspension of TS-1 is then acidified with HCl up to pH 4 and then mixed with a hydroalcoholic suspension of beta zeolite prepared by the dispersion of 4.3 g of the respective precursor in 30 ml of demineralized $H_2O$ and subsequent dilution with 60 ml of EtOH, according to the procedure described in example 5.

The composite material proves to consist of microspheres with the following characteristics:

median diameter ($D_{50}$ in $\mu$m)=59;

composition (weight %): beta zeolite=27; TS-1=29; $TiO_2$=1.11;

specific surface (S.S. in $m^2/g$):536.

EXAMPLES 7–10

With respect to example 6, the composition of the ternary composite materials is varied.

In the preparation of the hybrid sols the following were maintained constant:

the volumetric ratio $H_2O/EtOH$ (=1);

the total volume of the hydroalcoholic medium (=120 ml);

the volume of the silica sol (=50 ml).

The composition (weight %) and the characteristics of the materials are shown in Table 2.

TABLE 2

| EXAMPLE Nr. | Zeolite beta (%) | TS-1 (%) | $D_{50}$ ($\mu$m) | $TiO_2$ (%) | Ti/Al (moles) |
|---|---|---|---|---|---|
| 7 | 35 | 21 | 59 | 0.81 | 0.23 |
| 8 | 21 | 29 | 57 | 1.10 | 0.52 |
| 9 | 16 | 41 | 56 | 1.57 | 0.97 |
| 10 | 9 | 46 | 69 | 1.76 | 1.94 |

The materials synthesized according to the examples proved to consist of microspheres with a compact internal structure, regardless of the beta zeolite/TS-1 composition.

EXAMPLES 11–19

The mechanical resistance of the microspheres of the composite materials of examples 1–10, is evaluated by maintaining an aqueous suspension of these materials (0.3 g in 50 ml of demineralized $H_2O$) in an ultrasonic bath (Branson; type 2200; 47 kHz) for 120 minutes at a maximum temperature of 35° C.

A sample of TS-1 with a spherical morphology (3.18% by weight of $TiO_2$) prepared according to the method described in U.S. Pat. No. 4,859,785 was used as reference (example 19).

The results obtained are shown in Table 3.

TABLE 3

| EX. | Zeolite β(%) | TS-1 (%) | $D_{50}$ ($\mu$m) | $D_{90}/D_{10}$ | $(D_{90}-D_{10})/D_{50}$ |
|---|---|---|---|---|---|
| 11 | — | 55 | 68[74] | 2.80[2.84] | 0.89[0.94] |
| 12 | — | 23.6 | 47[52] | 2.38[2.61] | 0.89[1.00] |
| 13 | — | 39.3 | 53[54] | 2.47[2.52] | 0.92[0.97] |
| 14 | 55 | — | 54[58] | 2.52[2.80] | 0.89[0.99] |
| 15 | 35 | 21 | 58[59] | 2.08[2.05] | 0.75[0.74] |
| 16 | 21 | 29 | 56[57] | 2.65[2.40] | 0.97[0.89] |
| 17 | 16 | 41 | 56[56] | 2.61[2.63] | 0.92[0.99] |
| 18 | 9 | 46 | 68[69] | 2.58[2.58] | 0.84[0.85] |
| 19 (ref.) | — | 100 | 16[27] | 5.17[4.38] | 1.41[1.38] |

[]: Initial granulometric values.

From the Table, it can be seen that the median diameter ($D_{50}$) of the microspheres of the composite materials undergoes variations which are much smaller than those observed on the reference sample (example 19); in addition, the minimum variation in the adimensional ratios after treatment of the powders with ultrasounds, indicates that the granulometric distribution remains basically unchanged.

EXAMPLE 20

The catalytic activity of the composite material of example 1 is evaluated in the decomposition reaction of $H_2O_2$.

The sample of titanium silicalite was used as reference, obtained by calcination of the precursor of example 1 at 550° C. for 4 hours with a heating rate of 50° C./h; titer in $TiO_2$=3.82%.

The catalytic test was carried out at a constant temperature of 70° C. under the following conditions: 99 ml of demineralized $H_2O$ and 1.90 g of the sample of example 1 (concentration of Ti=5 mmoles/l) were charged into a 250 ml glass flask, equipped with a thermostat-regulated bath, reflux cooler and mechanical stirrer; the aqueous suspension of the material was thermostat-regulated under magnetic stirring at 70° C. and 1 ml of $H_2O_2$ (Merck; 30% by weight) was then added.

10 ml test samples were then taken over a period of time to determine the concentration of residual $H_2O_2$ with the iodometric method.

The semidecomposition time of the $H_2O_2$ ($t_{1/2}$=204 minutes) proved comparable to that of the reference sample ($t_{1/2}$=207 minutes) determined under analogous conditions at a concentration of 5 mmoles/l of Ti.

The presence of silica in the composite material did not alter the catalytic properties of the titanium silicalite.

EXAMPLES 21–23

The catalytic activity of the composite material of example 1 is evaluated in the epoxidation reaction of 1,3-butadiene in the presence of $H_2O_2$.

A jacketed cylindrical glass reactor (volume 150 ml) was used, equipped with: a thermostat-regulated bath, temperature and pH control, mechanical stirrer with a variable controlled rate, reflux condenser cooled by means of a thermocryostat to −25° C., feeding inlet of the solution of $H_2O_2$ and glass immersion tube for the feeding of the gaseous butadiene.

The dosage of the solution of $H_2O_2$ was carried out with a graded glass filter funnel and dosage pump; the 1,3-butadiene was fed from the cylinder, with a relative pressure reducer, placed on the balance and connected to the reactor with a "viton" line and flowmeter.

1.14 g of composite material of example 1 equal to 0.3 mmoles of Ti, 12 ml of demineralized $H_2O$ and 100 ml of methanol (Rudipont Reagent Grade; titer 99.9%), are charged into the reactor.

The reactor is heated to 40° C. and the pH corrected to 6.50 by dripping in an aqueous solution at 5% by weight of KOH.

The feeding of the reagents ($H_2O_2$ and butadiene) is initiated at 40° C. and under vigorous stirring (850 r.p.m.), maintaining the pH at 6.50 with periodical additions of the solution of KOH.

During the first 10 minutes 27 millimoles of $H_2O_2$ (Fluka; aqueous solution at 60% by weight) were fed; during the following 20 minutes, the feeding (133 millimoles) of the 1,3-butadiene (Aldrich; titer 99%) was completed.

The increases in pH were corrected to 6.50 with the addition of an 0.1 N solution of $H_2SO_4$, and the reaction was continued for a further hour at 40° C.

At the end the reaction products were separated from the catalyst by filtration under nitrogen pressure, and the filtrate collected in a container cooled with an external water and ice bath to avoid losses of the product.

The same operating procedure (0.3 millimoles of Ti) was adopted for examples 22 (using the composite material of example 2) and 23 (reference) using as catalyst the TS-1 of example 20.

The experimental results obtained are summarized in Table 4, in which:

$$-\text{yield} = \frac{100 \times (\text{mmoles of 1, 2-epoxy-3-butene obtained})}{(\text{mmoles of } H_2O_2 \text{ charged})}$$

$$-\text{select.} = \frac{100 \times (\text{mmoles of 1, 2-epoxy-3-butene obtained})}{\text{mmoles of } H_2O_2 (\text{charged} - \text{residual})}$$

The yields and selectivities obtained using the composite materials of the invention as catalysts are in line with those obtained with the reference standard.

TABLE 4

| EXAMPLE | Catalyst (TiO$_2$ weight %) | 1,2-Epoxy-3-butene (weight %) | Yield (%) | Selectivity (%) |
| --- | --- | --- | --- | --- |
| 21 | 2.1 | 1.02 | 66.6 | 67.2 |
| 22 | 0.9 | 0.86 | 67.9 | 68.5 |
| 23 (ref.) | 3.8 | 0.89 | 68.6 | 69.3 |

EXAMPLES 24–25

The catalytic activity of the composite material of example 1 is evaluated in the hydroxylation reaction of benzene to phenol with $H_2O_2$.

The sample of TS-1 of example 23 was used as reference.

A glass cylindrical reactor was used with a flat bottom (volume 30 ml) equipped with: magnetic stirrer, heating/cooling jacket, temperature control, reflux condenser cooled with running water, feeding inlet of the reagents.

The following products are charged into the reactor: 2.75 g (35 mmoles) of benzene (Fluka; titer>99.5%), 0.8 g (7 mmoles) of $H_2O_2$ (Rudipont; titer 33% w/v), 9 ml of methanol (Prolabo; titer>99.8%), 0.91 g of the composite material of example 1, corresponding to 0.24 mmoles of Ti.

The reaction mixture, maintained under magnetic stirring, is heated to reflux temperature for 4 hours (T=61° C.); then after rapid cooling, it is filtered on a filter with a porous septum.

The reaction raw product is subsequently diluted with acetonitrile (about 100 ml) and analyzed by HPLC chromatograph (Shimadzu) under the following conditions:

chromatographic column: LiChrospher 100 RP-18 end-capped (5 μm);

eluation: acetonitrile and aqueous solution 0.01 M of $H_3PO_4$;

temperature: 40° C.;

retention time of the phenol: 16 minutes.

In reference example 25 the same conditions were applied as for example 24, charging into the reactor 0.5 g of TS-1 (0.24 mmoles of Ti).

The results are shown in Table 5 in which:

$$-\text{yield } (\%) = \frac{100 \times (\text{mmoles of phenol})}{(\text{mmoles of benzene})}$$

$$-\text{selectivity } (\%) = \frac{100 \times (\text{mmoles of phenol})}{(\text{mmoles of reacted benzene})}$$

TABLE 5

| EXAMPLE | Catalyst (weight % TiO$_2$) | Yield (%) | Selectivity (%) |
| --- | --- | --- | --- |
| 24 | 2.1 | 3.3 | 86 |
| 25 (ref.) | 3.8 | 3.1 | 86 |

The catalytic behavior of the composite material silica/TS-1 in the hydroxylation reaction of benzene to phenol is comparable to that of the reference standard.

EXAMPLES 26–28

Example 24 is repeated using the ternary composite materials silica/titanium silicalite/beta zeolite of examples 6, 8 and 9.

A quantity of composite material equivalent to 0.24 mmoles of Ti was charged into the reactor.

The results are shown in Table 6.

TABLE 6

| EXAMPLE | Zeolite beta (%) | TS-1 (%) | Ti/Al (moles) | Yield (%) | Select. (%) |
| --- | --- | --- | --- | --- | --- |
| 26 | 27 | 29 | 0.41 | 4.0 | 100 |
| 27 | 21 | 29 | 0.52 | 4.5 | 100 |
| 28 | 16 | 41 | 0.97 | 3.1 | 100 |

Compared to titanium silicalite (example 25) and the binary material silica/titanium silicalite (example 24), the presence of beta zeolite in the ternary composite material significantly increases the selectivity and also the yield in the case of the compositions of examples 26 and 27.

What is claimed is:

1. Microspheres of a composite material consisting of:

(a) silica from 43 to 50 wt. %;

(b) beta zeolite from 9 to 35 wt %;

(c) titanium silicalite from 21 to 46 wt %;

the total percentage of (a), (b), and (c) being equal to 100%, and said microspheres having a specific surface value between 300 and 800 m$^2$/g and an average diameter of between 20 and 150 μm.

2. The microspheres of claim 1, wherein the sum of (b) plus (c) is between 50 and 70 wt %.

* * * * *

UNITED STATES PATENT AND TRADEMARK OFFICE
CERTIFICATE OF CORRECTION

PATENT NO. : 5,965,476

DATED : October 12, 1999

INVENTOR(S): Luigi BALDUCCI et al

It is certified that an error appears in the above-identified patent and that said Letters Patent is hereby corrected as shown below:

On the title page, item [30], should be:

--[30] Foreign Application Priority Data

Feb. 22, 1996    [IT] Italy..........MI 96 A 0330
    Sep. 6, 1996    [IT] Italy..........MI 96 A 1836--

Signed and Sealed this

Fourth Day of July, 2000

Attest:

Q. TODD DICKINSON

*Attesting Officer*      *Director of Patents and Trademarks*